United States Patent
Chen et al.

(10) Patent No.: US 8,298,141 B2
(45) Date of Patent: Oct. 30, 2012

(54) METHOD FOR MEASURING PHYSIOLOGICAL PARAMETERS

(75) Inventors: Tai Been Chen, Kaohsiung (TW); Yen Hsien Lee, Taoyuan County (TW); Mu Yu Tsai, Hsinchu (TW); Yu Jen Su, Kaohsiung (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 36 days.

(21) Appl. No.: 12/979,532

(22) Filed: Dec. 28, 2010

(65) Prior Publication Data

US 2012/0165690 A1  Jun. 28, 2012

(30) Foreign Application Priority Data

Dec. 24, 2010  (TW) .............................. 99145712 A

(51) Int. Cl.
*A61B 5/00* (2006.01)

(52) U.S. Cl. ...................................... 600/300
(58) Field of Classification Search ............. 600/509, 600/544; 701/1
See application file for complete search history.

(56) References Cited

U.S. PATENT DOCUMENTS

| | | | |
|---|---|---|---|
| 4,513,748 A | 4/1985 | Nowogrodzki et al. | |
| 5,738,104 A | 4/1998 | Lo et al. | |
| 5,876,350 A | 3/1999 | Lo et al. | |
| 6,096,061 A * | 8/2000 | Alt et al. | 607/4 |
| 6,577,269 B2 | 6/2003 | Woodington et al. | |
| 7,107,094 B2 | 9/2006 | Huang et al. | |
| 7,135,002 B2 | 11/2006 | Sullivan | |
| 7,245,960 B2 | 7/2007 | Yasushi et al. | |
| 7,643,873 B2 | 1/2010 | Chan | |
| 7,725,150 B2 | 5/2010 | Tupin, Jr. et al. | |
| 7,738,949 B2 | 6/2010 | Holland | |
| 2004/0138580 A1* | 7/2004 | Frei et al. | 600/544 |
| 2008/0009685 A1 | 1/2008 | Kim et al. | |
| 2010/0152600 A1 | 6/2010 | Droitcour et al. | |
| 2010/0179421 A1 | 7/2010 | Tupin | |
| 2010/0179438 A1 | 7/2010 | Heneghan et al. | |

FOREIGN PATENT DOCUMENTS

| | | |
|---|---|---|
| TW | 228981 B | 3/2005 |
| TW | 200616584 | 6/2006 |
| TW | 200908932 | 3/2009 |

* cited by examiner

*Primary Examiner* — George Manuel
*Assistant Examiner* — Robert N Wieland
(74) *Attorney, Agent, or Firm* — Egbert Law Offices, PLLC

(57) ABSTRACT

A method for measuring physiological parameters uses statistical properties, spectrum analysis and feedback mechanisms to remove the signal noise generated by human body movement from a detected physiological signal.

39 Claims, 7 Drawing Sheets

METHOD FOR MEASURING PHYSIOLOGICAL PARAMETERS

BACKGROUND OF THE DISCLOSURE

1. Field of the Disclosure

The present disclosure relates to a method for measuring physiological parameters.

2. Description of the Related Art

As people pay more and more attention to health, increasing numbers of physiological tests are conducted in non-hospital settings. If the subject base is expanded from hospital patients to include all people, that is, if technologies for detecting physiological parameters are applied to daily life activities of subjects, many conditions may be avoided. For example, if heartbeat or breathing of a subject is monitored during sleep, an apnea syndrome may be prevented. If the heartbeat or breathing of the subject can be monitored while driving, car accidents due to drowsiness can be prevented.

Based on the above situation, various detection technologies for measuring physiological parameters are available in the industry. Such technologies include exploiting spectral conversion to calculate heartbeat rate, applying a chest strap-type heart rate monitor to monitor the subject's electrocardiogram during exercise, applying different filters to an electrocardiogram detection result to remove noise caused by circuit and electromyographic signals, employing Doppler radar during heartbeat and breathing monitoring, estimating the heartbeat rate through spectral conversion in a recursive fashion, and using a pressure gauge and spectral conversion to normalize heartbeat rate during exercising.

Accurate measurement of heartbeat and breathing rate are usually only possible when the subject is not in motion. If, during the measurement process, the subject is in motion, a floating signal occurs in the electrocardiogram detector due to the interference of the electromyographic signal. Radar sensors also are affected by interference caused by relative movement of the subject. However, the prior art has not provided any method for removing the signal interference caused by the subject's movement.

Based on the above, in order to solve the problem currently faced by the medical industry, namely, the imprecise measurement of physiological parameters due to human body motion or movement interference, it is necessary to design a method for measuring physiological parameters. The to method is capable of removing noise generated from movement interference through statistical properties, spectrum analysis and feedback mechanisms. The present disclosure provides the method for measuring physiological parameters.

SUMMARY OF THE DISCLOSURE

The present disclosure presents a method for measuring physiological parameters, which includes the steps of: continuously receiving a physiological signal, where the physiological signal includes at least one physiological parameter of a subject; calculating a statistical parameter of the physiological signal; determining whether the physiological signal includes movement interference noise according to the statistical parameter; if it is determined that the received signal includes the movement interference noise, reduce the movement interference noise; decide a maximum value of the physiological signal on a frequency spectrum through a Fast Fourier Transform; and decide at least one physiological parameter of the subject accordingly.

Technical features of the present disclosure are briefly described, and may be better understood through detailed descriptions below. Other technical features forming the subject matter of the present disclosure are also described. Persons with ordinary skill in the art of the present disclosure shall understand that modifications or designs of other structures or manufacturing procedures based on the concepts and specific exemplary embodiments disclosed below can be applied to meet the objectives of the present disclosure. Persons with ordinary skill in the art of the present disclosure shall also understand that such equivalent constructions do not depart from the spirit and scope of the present disclosure.

BRIEF DESCRIPTION OF THE DRAWINGS

The Disclosure will be described according to the appended drawings in which.

DETAILED DESCRIPTION OF THE DISCLOSURE

The disclosure is directed to a method for measuring physiological parameters. For thorough understanding of the disclosure, detailed steps are provided in the following description. The implementation of the disclosure is not limited to special details familiar to those skilled in the art of the disclosure. In addition, steps known to all are not described in detail, so as to avoid unnecessary limitation to the disclosure. The preferred exemplary embodiments of the disclosure are described below. However, in addition to the detailed description, the disclosure may further be implemented in other exemplary embodiments. The scope of the disclosure is not limited, and is subject to the scope of the claims below.

Figure 1:
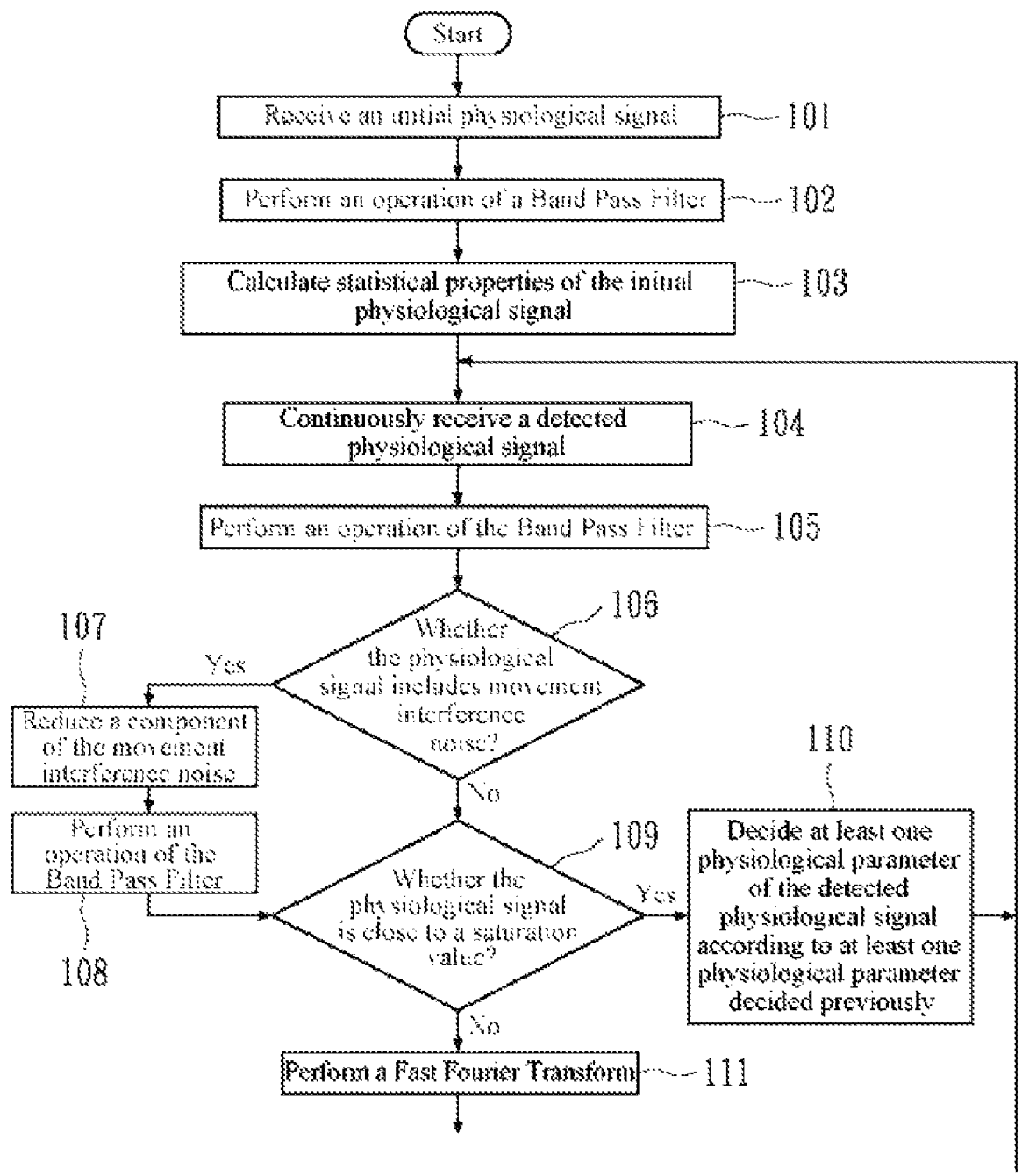
FIG. 1 is a flowchart of a method for measuring physiological parameters according to one exemplary embodiment of the present disclosure.
Figure 1:
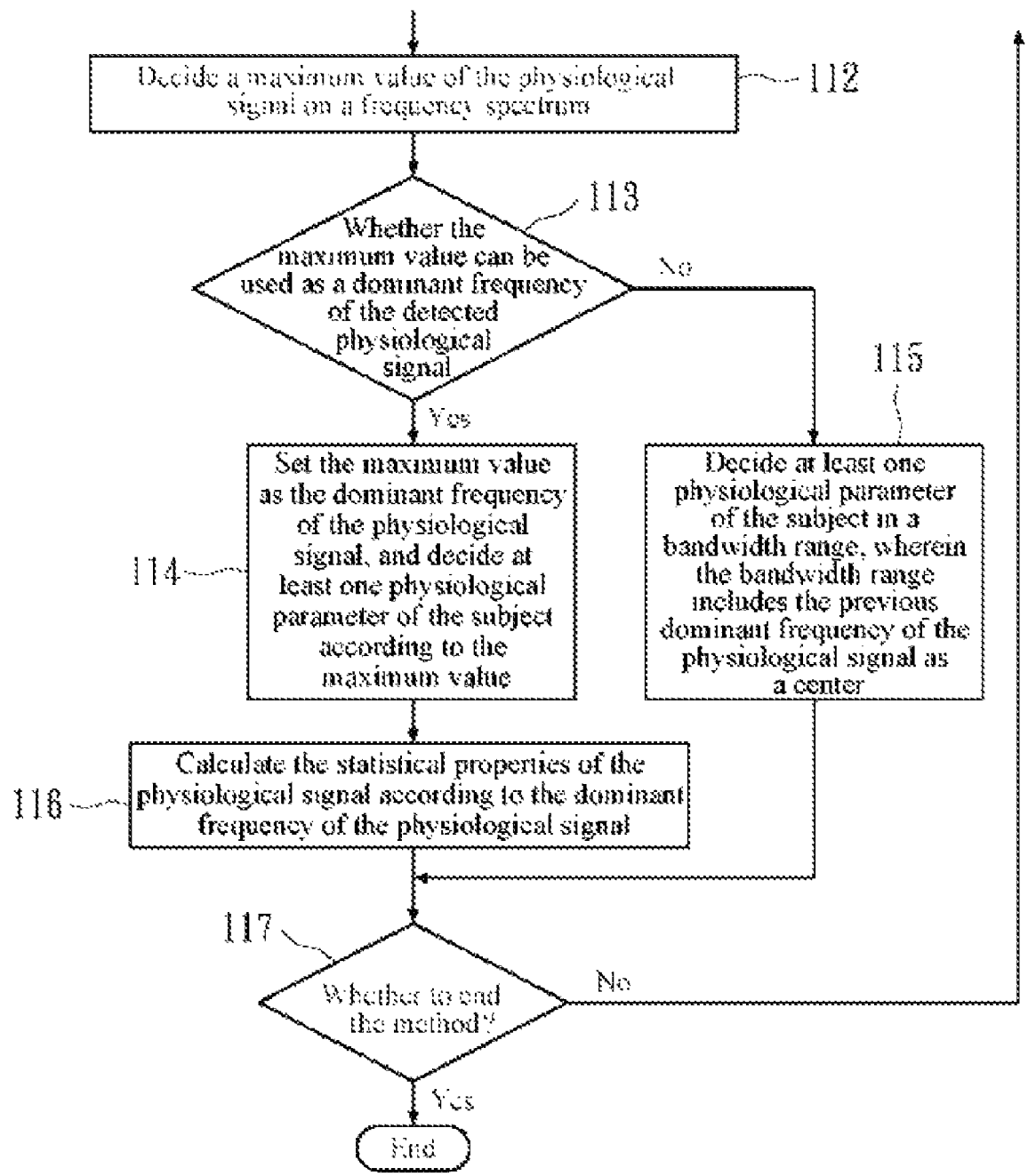

FIG. 1 is a flow chart of a method for measuring physiological parameters according to an exemplary embodiment of the disclosure. In Step 101, an initial physiological signal is received, where the physiological signal includes at least one physiological parameter of a subject, and Step 102 is executed. In Step 102, an operation of a bandpass filter is performed on the initial physiological signal, and Step 103 is executed. In Step 103, statistical properties of the initial physiological signal are calculated, and Step 104 is executed. In some exemplary embodiments of the disclosure, the calculated statistical properties include an average value and a standard deviation of the initial physiological signal. In Step 104, an initial physiological signal is continuously received, where the physiological signal includes at least one physiological parameter of the subject, and Step 105 is executed. In some exemplary embodiments of the disclosure, the initial physiological signal and the detected physiological signal are received and stored in a queue. In some exemplary embodiments of the disclosure, the at least one physiological parameter includes a breath parameter, a heartbeat parameter or an enterocinesia parameter of the subject. In Step 105, an operation of the bandpass filter is performed on the detected physiological signal, and Step 106 is executed.

In Step 106, it is determined whether the detected physiological signal includes movement interference noise according to the calculated statistical properties. If it is determined that the detected physiological signal includes the movement interference noise, then Step 107 is executed; otherwise, if it is determined that the detected physiological signal does not include the movement interference noise, then Step 109 is executed. In some exemplary embodiments of the present disclosure, it is determined in Step 106 whether a difference between each sampling point of the detected physiological signal and an average value of the physiological signal is greater than an integral multiple of a standard deviation of the physiological signal. The integral multiple, for example, can be 1 to 5. In Step 106, it is determined whether the received signal includes the movement interference noise. In Step 107, a component of the movement interference noise is reduced, and Step 108 is executed. In some exemplary embodiments of the present disclosure, in Step 107, the step of reducing the movement interference noise is performed to reduce an influence of the movement interference noise on the frequency spectrum. In some exemplary embodiments of the present disclosure, the step of reducing the movement interference noise is performed to perform a calculation on the physiological signal using a Chebyshev Inequality. However, the step of reducing the movement interference noise of the present disclosure is not limited to using the Chebyshev Inequality, but may include any operation method capable of reducing the movement interference noise, for example, a bandpass filter, a Median Filter or a Gaussian Filter. Among such operation methods, the Chebyshev Inequality is a relatively reliable and effective operation method. In Step 108, an operation of the bandpass filter is performed on the detected physiological signal with the reduced movement interference noise, and Step 109 is executed.

In Step 109, it is determined whether the detected physiological signal is close to a saturation value. If it is determined that the detected physiological signal is close to the saturation value, then Step 110 is executed. If it is determined that the detected physiological signal is not close to the saturation value, then Step 111 is executed. In Step 110, at least one physiological parameter of the detected physiological signal is decided according to the at least one physiological parameter decided previously. In Step 111, a power spectral density of the detected physiological signal is calculated using the Fast Fourier Transform, and Step 112 is executed. In some exemplary embodiments of the present disclosure, in Step 111, the step of calculation using the Fast Fourier Transform is performed according to a specific timeframe after deducting the average value from the detected physiological signal. In some exemplary embodiments of the present disclosure, the specific timeframe is from 1 to 60 seconds. In Step 112, a maximum value of the detected physiological signal on the frequency spectrum is determined, and Step 113 is executed. In Step 113, it is determined whether the maximum value can be used as a dominant frequency of the detected physiological signal. If it is determined that the maximum value can be used as the dominant frequency of the detected physiological signal, then Step 114 is executed. If it is determined that the maximum value cannot be used as the dominant frequency of the detected physiological signal, then Step 115 is executed. In some exemplary embodiments of the present disclosure, in Step 113, a second maximum value is searched in a bandwidth range, wherein the bandwidth range includes the maximum value as a center, and it is determined whether energy of the maximum value is greater than an integral multiple of energy of the second maximum value. If the energy of the maximum value is greater than the integral multiple of the energy of the second maximum value, it is determined that the maximum value can be used as the dominant frequency of the detected physiological signal. In some exemplary embodiments of the present disclosure, the bandwidth range in Step 113 is between 0 and 4 hertz (Hz). In some exemplary embodiments of the present disclosure, the integral multiple in Step 113 is between 1 and 20.

In Step 114, the maximum value is set as the dominant frequency of the physiological signal, at least one physiological parameter of the subject is decided according to the maximum value, and Step 116 is executed. In Step 115, at least one physiological parameter of the subject is decided in a bandwidth range, wherein the bandwidth range includes the previous dominant frequency of the physiological signal as a center, and Step 117 is executed. In some exemplary embodiments of the present disclosure, the bandwidth range of Step 115 is between 0 and 4 Hz. In Step 116, the statistical properties of the physiological signal are calculated according to the dominant frequency of the physiological signal, and Step 117 is executed. In Step 117, it is determined whether to end the method. If it is determined to end the method, the method is ended. If it is determined not to end the method, the process returns to Step 104.

Figure 2:
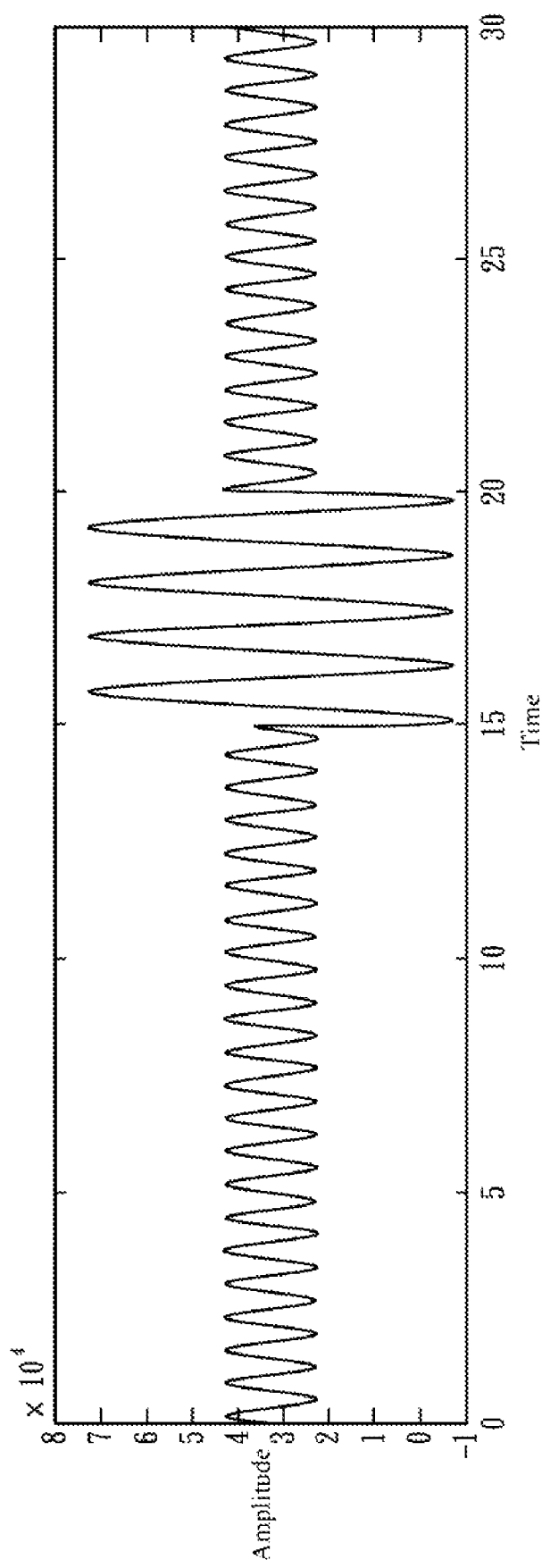
FIG. 2 is a time domain chart of a detected physiological signal according to one exemplary embodiment of the present disclosure.
Figure 3:
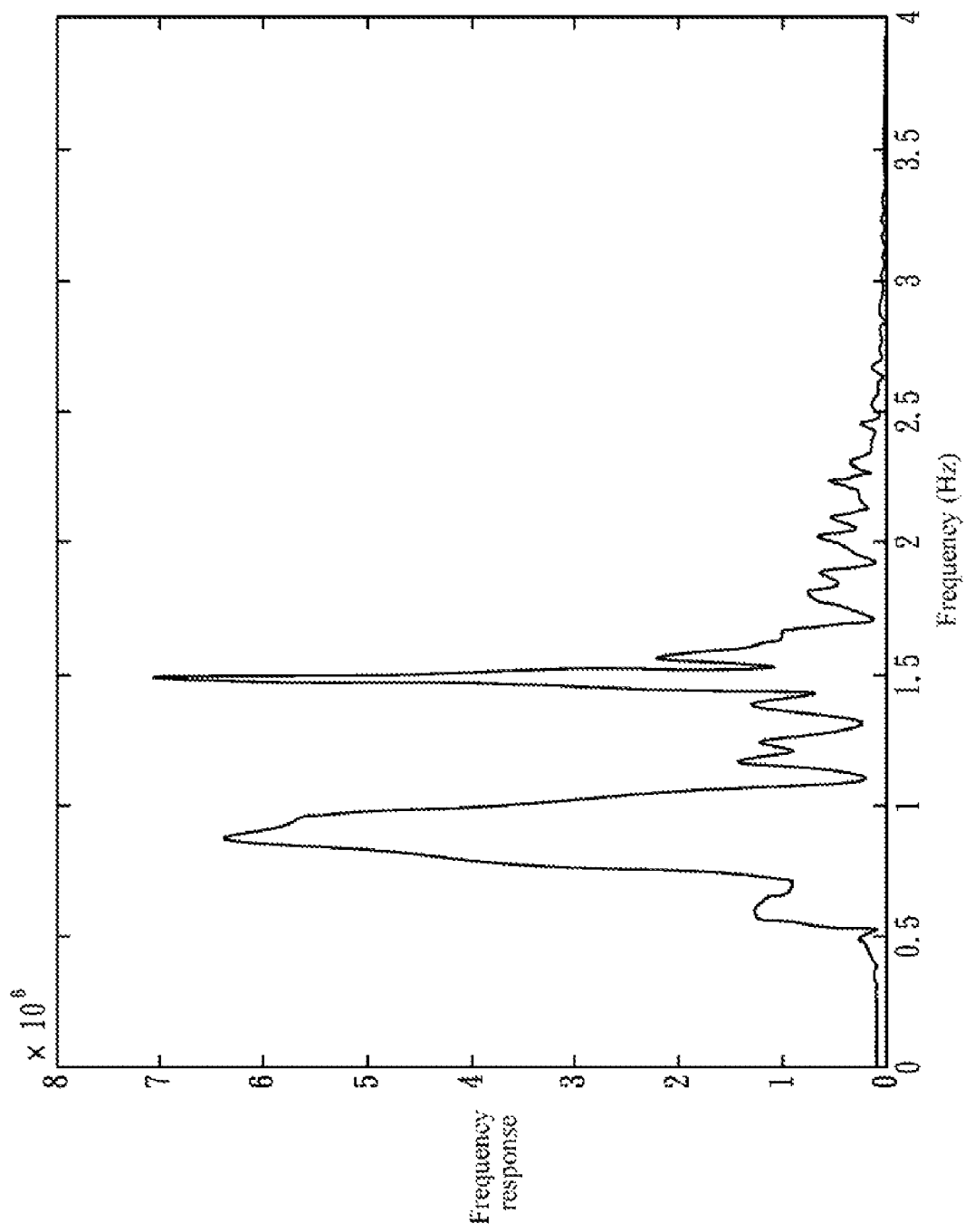
FIG. 3 is a frequency domain chart of a detected physiological signal according to one exemplary embodiment of the present disclosure.

In the following example, the method of FIG. 1 is applied to detecting a physiological parameter. FIG. 2 is a time domain chart of a detected physiological signal according to an exemplary embodiment of the present disclosure, where the detected physiological signal includes a heartbeat signal and a movement interference signal. In the exemplary embodiment, the physiological signal may be provided by an electrocardiogram or an ultra wideband signal detector. The detected physiological signal is a time domain chart after the operation of the bandpass filter in Step 105. As shown in FIG. 2, a large amplitude is generated in a middle section of the detected physiological signal due to movement interference. FIG. 3 is the frequency domain chart of the detected physiological signal in FIG. 2. As shown in FIG. 3, the heartbeat signal is a heart rate wave of 1.5 Hz and the movement interference signal is 0.9 Hz. Therefore, a high frequency response exists at both 1.5 Hz and 0.9 Hz in the frequency domain chart of the detected physiological signal.

Figure 4:
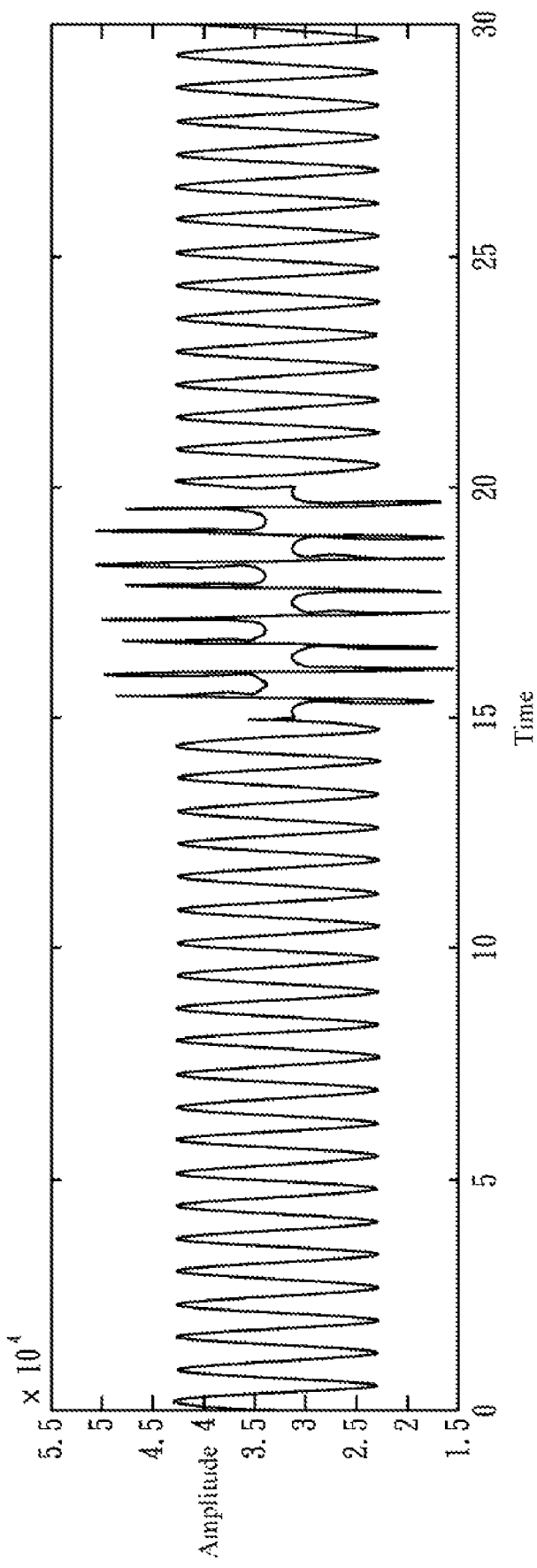
FIG. 4 is a time domain chart of a detected physiological signal after an operation of reducing movement interference noise according to one exemplary embodiment of the present disclosure.

In Step 106, if it is determined that the detected physiological signal includes the movement interference noise, then Step 107 is executed. In Step 107, calculation is performed on the detected physiological signal using the Chebyshev Inequality in order to reduce the component of the movement interference noise. FIG. 4 is a time domain chart of the detected physiological signal after the calculation of the Chebyshev Inequality. As shown in FIG. 4, the operation of the Chebyshev Inequality is to compress a part of the detected physiological signal influenced by the movement interference signal, namely, the signal at the middle section of the chart. A part with higher amplitude is compressed at a higher degree. As for the frequency domain, the calculation of the Chebyshev Inequality is equivalent to moving a component at 0.9 Hz of the physiological signal to a high-frequency position.

Figure 5:
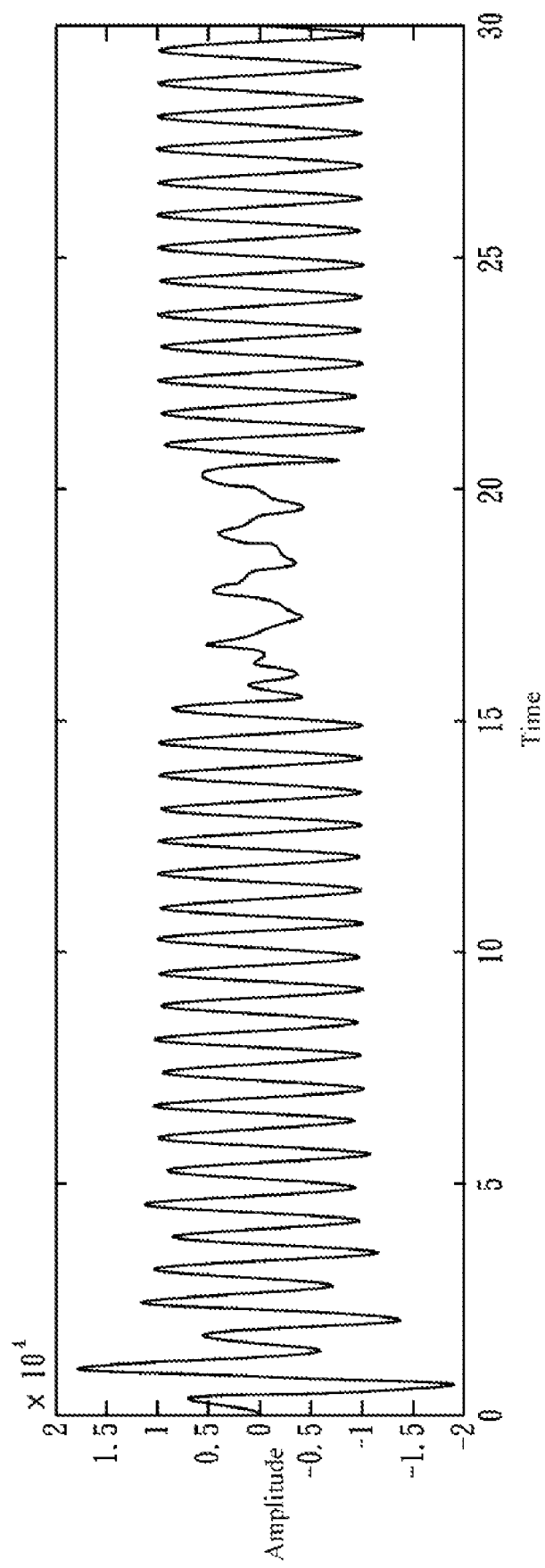
FIG. 5 is a time domain chart of a detected physiological signal after an operation of reducing movement interference noise and an operation of a bandpass filter according to one exemplary embodiment of the present disclosure.
Figure 6:
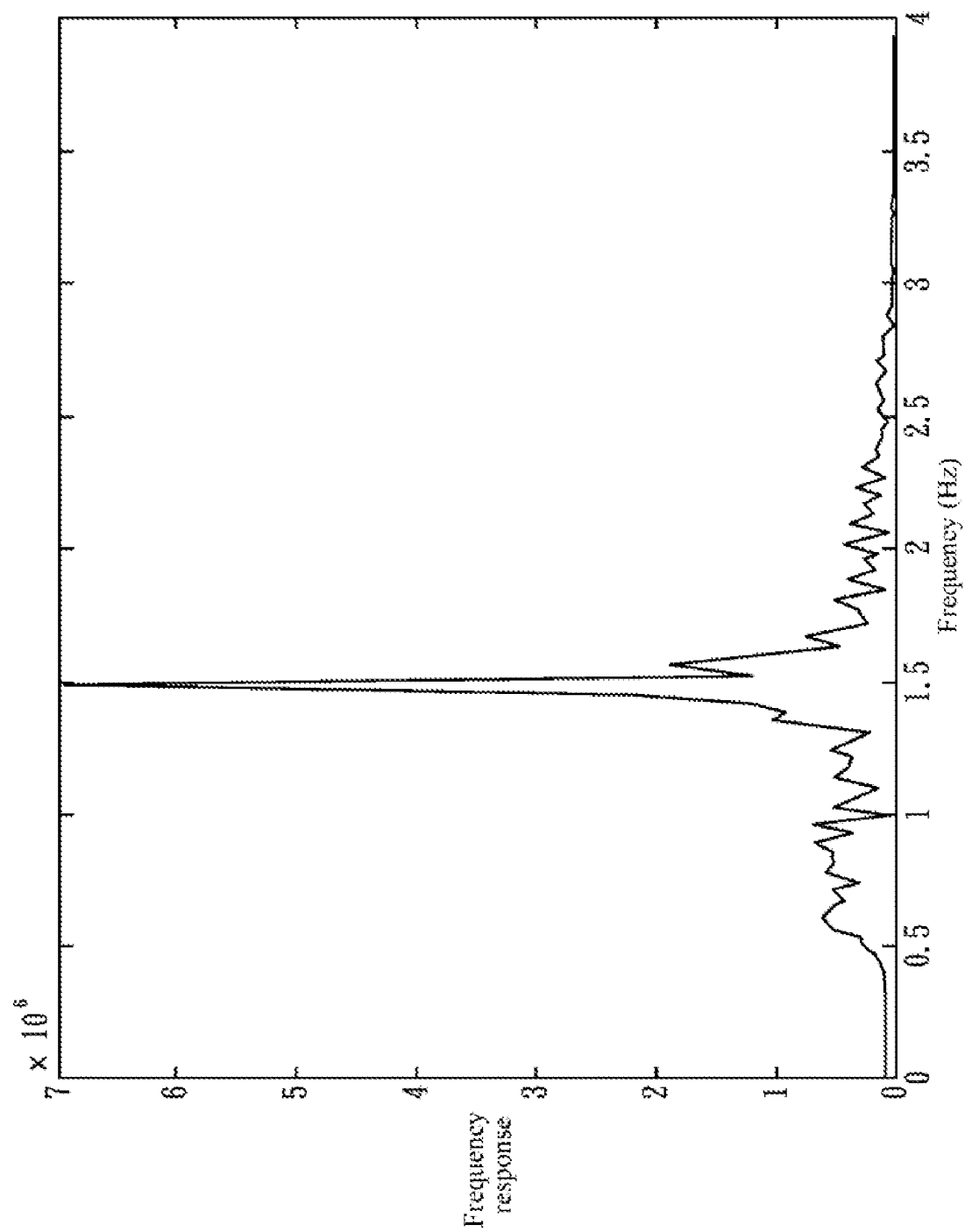
FIG. 6 is a frequency domain chart of a detected physiological signal after an operation of reducing movement interference noise and an operation of a bandpass filter according to one exemplary embodiment of the present disclosure.

In Step 108, the operation of the bandpass filter is performed on the detected physiological signal. In this step, the movement interference noise of the detected physiological signal is reduced. FIG. 5 is a time domain chart of the detected physiological signal using the operation of the bandpass filter after the calculation of the Chebyshev Inequality. As shown in FIG. 5, a high-frequency component generated by the calculation of Chebyshev Inequality, namely a sharp-pointed section of the detected physiological signal in FIG. 4, is eliminated from the detected physiological signal. FIG. 6 is a frequency domain chart of the detected physiological signal through the operation of the bandpass filter after the calculation of the Chebyshev Inequality. As shown in FIG. 6, the movement interference signal is moved to the high-frequency position, and is eliminated through the operation of the bandpass filter. Therefore, the detected physiological signal only includes the detected heartbeat signal.

In Step 109, if the detected physiological signal is close to the saturation value, that is, if some of the sampling points of the detected physiological signal reach the saturation value, then the detected physiological signal is not reliable, and Step 110 is executed. In Step 110, the previously decided heartbeat parameter is directly output.

In Step 113, if the noise of the detected physiological signal is removed, then only one dominant maximum value remains in a bandwidth range, and it is determined that the maximum value can be used as the dominant frequency of the detected physiological signal. On the other hand, if some noise still exists in the detected physiological signal, then other noise components remain in the bandwidth range, and it is determined that the maximum value cannot be used as the dominant frequency of the detected physiological signal.

In Step 116, if it is determined that the maximum value can be used as the dominant frequency of the detected physiological signal, the statistical parameter of the physiological signal is updated accordingly. This is a feedback mechanism provided by the method for measuring physiological parameters according to the present disclosure. According to the feedback mechanism, the method for measuring physiological parameters of the present disclosure is capable of continuously tracing the physiological parameters of the subject.

In conclusion, the method for measuring physiological parameters according to the present disclosure uses statistical, properties, spectrum analysis and feedback mechanisms to perform signal processing on the detected physiological signal. As shown in the above description, the method for measuring physiological parameters of the present disclosure is capable of removing noise generated from the movement interference.

Technical content and technical features of the present disclosure are disclosed. However, persons skilled in the art may make other replacements and modifications without departing from the spirit of the present disclosure. Therefore, the scope of the present disclosure shall not be limited to the exemplary embodiments disclosed. Rather, the scope of the present disclosure should include all replacements and modifications without departing from the present disclosure and shall be covered by the scope of claims below.

What is claimed is:

1. A method for measuring physiological parameters, the method comprising the steps of:
    continuously receiving a physiological signal, wherein the physiological signal comprises at least one physiological parameter of a subject;
    calculating a statistical parameter of the physiological signal;
    determining whether the physiological signal comprises movement interference noise according to the statistical parameter;
    reducing the movement interference noise if it is determined that the received signal comprises the movement interference noise;
    calculating a maximum value of the physiological signal on a frequency spectrum using a Fast Fourier Transform, and deciding at least one physiological parameter of the subject according to the step of calculating the maximum value;
    deciding the maximum value of the physiological signal on the frequency spectrum using the Fast Fourier Transform; and
    determining whether the maximum value is able to be used as a dominant frequency of the physiological signal.

2. The method according to claim 1, wherein the step of calculating the maximum value comprises the steps of:
    repeating the step of calculating the statistical parameter of the physiological signal if the maximum value of the physiological signal is able to be used as the dominant frequency of the physiological signal, and deciding at least one physiological parameter of the subject according to the maximum value; and
    deciding at least one physiological parameter of the subject in a first bandwidth range, wherein the first bandwidth range includes a previous dominant frequency of the physiological signal as a center, if the maximum value is not able to be used as the dominant frequency of the physiological signal.

3. The method according to claim 1, wherein the physiological signal is received and stored in a queue.

4. The method according to claim 1, wherein an operation of a bandpass filter is performed on the physiological signal after being received.

5. The method according to claim 1, further comprising the steps of:
    determining whether the physiological signal is close to a saturation value; and
    deciding at least one physiological parameter of the physiological signal to be the at least one physiological parameter decided previously if the physiological signal is close to a saturation value.

6. The method according to claim 1, wherein the step of determining comprises determining whether a difference between each sampling point of the physiological signal and an average value of the physiological signal is greater than an integral multiple of a standard deviation of the physiological signal; if the difference is greater than the integral multiple of the standard deviation of the physiological signal, then the received signal is determined to include the movement interference noise.

7. The method according to claim 6, wherein the integral multiple is in a range from 1 to 5.

8. The method according to claim 1, wherein the step of reducing comprises reducing an influence from the movement interference noise on the frequency spectrum.

9. The method according to claim 1, wherein the step of reducing comprises performing calculation on the physiological signal using a Chebyshev Inequality.

10. The method according to claim 9, wherein an operation of the bandpass filter is performed on the physiological signal after the operation of the Chebyshev Inequality.

11. The method according to claim 1, wherein the step of deciding using the Fast Fourier Transform comprises performing the Fast Fourier Transform according to a specific timeframe after deducting an average value from the physiological signal.

12. The method according to claim 11, wherein the specific timeframe is from 1 to 60 seconds.

13. The method according to claim 2, wherein the step of deciding at least one physiological parameter of the subject in the first bandwidth range takes a maximum value as a center, and determining whether energy of the maximum value is greater than an integral multiple of energy of the second maximum value; if the energy of the maximum value is greater than the integral multiple of the energy of the second maximum value, then the maximum value is able to be used as the dominant frequency of the physiological signal.

14. The method according to claim 13, wherein the second bandwidth range is between 0 and 4 Hz.

15. The method according to claim 13, wherein the integral multiple is in a range of 1 to 20.

16. The method according to claim 2, wherein the first bandwidth range is between 0 and 4 Hz.

17. The method according to claim 1, wherein the at least one physiological parameter comprises a heartbeat parameter of the subject.

18. The method according to claim 1, wherein the at least one physiological parameter comprises a breath parameter of the subject.

19. The method according to claim 1, wherein the at least one physiological parameter comprises an enterocinesia parameter of the subject.

20. The method according to claim 1, wherein the physiological signal is provided by an electrocardiogram or an ultra wideband signal detector.

21. A method for measuring physiological parameters, the method comprising the steps of:
continuously receiving a physiological signal, wherein the physiological signal comprises at least one physiological parameter of a subject;
calculating a statistical parameter of the physiological signal;
determining whether the physiological signal comprises movement interference noise according to the statistical parameter;
reducing the movement interference noise if it is determined that the received signal comprises the movement interference noise; and
calculating a maximum value of the physiological signal on a frequency spectrum using a Fast Fourier Transform, and deciding at least one physiological parameter of the subject according to the step of calculating a maximum value;
wherein the determining step is to determine whether a difference between each sampling point of the physiological signal and an average value of the physiological signal is greater than an integral multiple of a standard deviation of the physiological signal; if the difference is greater than the integral multiple of the standard deviation of the physiological signal, then the received signal is determined to include the movement interference noise.

22. The method according to claim 21, wherein the step of calculating the maximum value comprises the steps of:
deciding the maximum value of the physiological signal on the frequency spectrum using the Fast Fourier Transform;
determining whether the maximum value is able to be used as a dominant frequency of the physiological signal;
repeating the step of calculating the statistical parameter of the physiological signal if the maximum value of the physiological signal is able to be used as the dominant frequency of the physiological signal, and deciding at least one physiological parameter of the subject according to the maximum value; and
deciding at least one physiological parameter of the subject in a first bandwidth range, wherein the first bandwidth range includes a previous dominant frequency of the physiological signal as a center, if the maximum value is not able to be used as the dominant frequency of the physiological signal.

23. The method according to claim 21, wherein the physiological signal is received and stored in a queue.

24. The method according to claim 21, wherein an operation of a bandpass filter is performed on the physiological signal after being received.

25. The method according to claim 21, further comprising the steps of:
determining whether the physiological signal is close to a saturation value; and
deciding at least one physiological parameter of the physiological signal to be the at least one physiological parameter decided previously if the physiological signal is close to a saturation value.

26. The method according to claim 25, wherein the integral multiple is in a range from 1 to 5.

27. The method according to claim 21, wherein the step of reducing comprises reducing an influence from the movement interference noise on the frequency spectrum.

28. The method according to claim 21, wherein the step of reducing comprises performing calculation on the physiological signal using a Chebyshev Inequality.

29. The method according to claim 28, wherein an operation of the bandpass filter is performed on the physiological signal after the operation of the Chebyshev Inequality.

30. The method according to claim 21, wherein the step of deciding using the Fast Fourier Transform comprises performing the Fast Fourier Transform according to a specific timeframe after deducting an average value from the physiological signal.

31. The method according to claim 30, wherein the specific timeframe is from 1 to 60 seconds.

32. The method according to claim 22, wherein the physiological parameter deciding step in the first bandwidth range takes a maximum value as a center, and determining whether energy of the maximum value is greater than an integral multiple of energy of the second maximum value;
if the energy of the maximum value is greater than the integral multiple of the energy of the second maximum value, then the maximum value is able to be used as the dominant frequency of the physiological signal.

33. The method according to claim 32, wherein the second bandwidth range is between 0 and 4 Hz.

34. The method according to claim 32, wherein the integral multiple is in a range of 1 to 20.

35. The method according to claim 22, wherein the first bandwidth range is between 0 and 4 Hz.

36. The method according to claim 21, wherein the at least one physiological parameter comprises a heartbeat parameter of the subject.

37. The method according to claim 21, wherein the at least one physiological parameter comprises a breath parameter of the subject.

38. The method according to claim 21, wherein the at least one physiological parameter comprises an enterocinesia parameter of the subject.

39. The method according to claim 21, wherein the physiological signal is provided by an electrocardiogram or an ultrawide band signal detector.

* * * * *